United States Patent [19]

Milner

[11] 4,323,509
[45] Apr. 6, 1982

[54] PROCESS FOR THE PREPARATION OF ALKYL FURANS

[75] Inventor: David J. Milner, Manchester, England

[73] Assignee: Imperial Chemical Industries Limited, London, England

[21] Appl. No.: 262,775

[22] Filed: May 11, 1981

[30] Foreign Application Priority Data

Jun. 11, 1980 [GB] United Kingdom ............... 19152/80

[51] Int. Cl.³ .......................................... C07D 307/28
[52] U.S. Cl. ............................................... 260/346.11
[58] Field of Search .................................... 260/346.11

[56] References Cited

U.S. PATENT DOCUMENTS 3,251,847   5/1966   Landis et al. .............. 260/346.11 X
3,833,677   9/1974   Grard ......................... 260/346.11 X

OTHER PUBLICATIONS

Olah, ed., Friedel-Crafts and Related Reactions, Interscience Publishers, New York (1964), pp. 104, 105 and 433.
Brown et al., Canadian Journal of Chemistry, vol. 35 (1957), pp. 236–250.

*Primary Examiner*—Richard Raymond
*Attorney, Agent, or Firm*—Cushman, Darby & Cushman

[57] ABSTRACT

A process for the preparation of alkyl furans which comprises reacting furan with an alkyl halide in the presence of iron (III) oxide and an iron (II) halide or iron (III) halide as catalyst.

7 Claims, No Drawings

PROCESS FOR THE PREPARATION OF ALKYL FURANS

This invention relates to a process for the preparation of alkylfurans.

The attempted alkylation of furan by the conventional Friedel-Crafts reaction using an alkyl halide or an alkene as alkylating agent and a Friedel-Crafts catalyst such as aluminum chloride or boron trifluoride etherate gives very poor yields.

For example, W. H. Brown and G. F. Wright, Canadian Journal of Chemistry, 35,236 (1957), obtained only 2.8% of 2-tert.butylfuran and a 4.0% yield of 2,5-di-tert.butylfuran by the action of isobutene on furan in the presence of boron trifluoride etherate.

The difficulties attendant upon alkylation of furan are also mentioned in "Friedel-Crafts and Related Reactions" edited by G. A. Olah, published 1964 by Interscience Publishers, Volume II, page 104, where it is stated: "Resinification of furan in the presence of Friedel-Crafts catalysts occurs quite readily. No doubt it is for this reason that very few alkylation reactions of furan have been reported"; and at page 433: "Successful alkylations of heterocyclic compounds are very rare."

It has now been found that much improved yields of alkylfurans by the direct alkylation of furan can be obtained in the presence of certain iron compounds.

According to the present invention there is provided a process for the preparation of alkylfurans which comprises reacting furan with an alkyl halide in the presence of iron (III) oxide and an iron (II) halide or iron (III) halide as catalyst.

The amount of iron (III) oxide which is used as catalyst is not critical and may be from 0.01 to 2.0 mols per mol of furan. It is convenient to use approximately 1.0 mol of iron (III) oxide per mol of furan. The use of a higher ratio than this may result in slightly improved yields but is offset by the considerable bulk of the iron oxide relative to the other reactants, which may give rise to filtration difficulties.

The iron (II) halide or iron (III) halide co-catalyst is employed in the minimum amount necessary to initiate the reaction, and from 0.01 to 0.05 mol per mol of furan may be used. It is preferred to use approximately 0.025 mols per mol of furan since this gives an acceptable balance between yields of product and rate of reaction. Excess of iron halide is to be avoided as it leads to lower yield of alkyl furan due to resinification of the furan starting material.

Furan is alkylated in the 2- and 2,5-positions, and if the dialkylated product is required then at least 2.0 and preferably 2.5 mols of alkyl halide per mol of furan are needed. Use of more than 2.5 mols of alkyl halide is not harmful and may result in an improved yield of dialkylated product, but against this must be set the additional cost of the excess halide, or, if the excess is to be recovered, the cost of recovery.

The use of less than 2 mols of alkyl halide per mol of furan results in the formation of a mixture of 2-alkyl- and 2,5-dialkylfurans which may be separated by, for example, preparative gas-liquid chromatography.

The reaction may be carried out in the absence of a solvent, but it is preferred to use a halogenated hydrocarbon solvent, for example, 1,1,1-trichloroethane or preferably dichloromethane.

Examples of the alkyl halides which may be used are tert.butyl chloride and tert.butyl bromide.

Examples of the iron (II) halide and iron (III) halide co-catalysts which may be used are iron (II) chloride, iron (II) bromide, iron (III) chloride and iron (III) bromide. The preferred co-catalyst is iron (III) chloride.

The reaction is preferably carried out by pre-mixing the furan and the alkyl halide and adding the mixture gradually, conveniently during about 1.5 hours, to the catalyst suspended in the solvent at the reaction temperature, which is conveniently the reflux temperature of the solvent. It is preferred to give the reaction mixture a further period of about 1.5 hours at reflux temperature, after which the catalyst is filtered off and the solvent is removed from the filtrate by evaporation or preferably by distillation. The product may then be isolated from the residue by distillation under reduced pressure. In order to keep the distillation residues mobile during the latter stages of the distillation, it is preferred to add a high-boiling solvent to the crude material before distillation commences. A convenient solvent for this purpose is glycerol. Other methods of operating the process are possible, for example, the solvent, reactants and catalyst may simply be mixed together and heated, but the preferred technique indicated above gives an easily controlled reaction.

2,5-Di-tert.butylfuran is useful as an intermediate in the preparation of certain fungicides such as are described in German Offenlegungsschrift No. 2819879. 2-Tert.butylfuran may be further alkylated by Friedel-Crafts reaction with a tert.butyl halide, to give 2,5-di-tert.butylfuran.

The invention is illustrated by the following Examples in which percentages are by weight.

EXAMPLE 1

Iron (III) oxide (3.0g ; BDH 85% grade) was stirred and heated under reflux (60° C.) with a mixture of furan (5.1g ; 75 m mol), tert.butyl chloride (28g ; 300 m mol) and 1,1,1-trichloroethane (sufficient to bring the total volume of liquids to 100 ml).

There was no reaction at first but when iron (III) chloride (0.4g) was added to the mixture there was an almost immediate start to the alkylation as indicated by the evolution of hydrogen chloride. 30 minutes after the addition of the iron (III) chloride the reaction mixture was cooled. The volume of liquid was 95 ml and glc analysis indicated that it contained 2,5-di-tert.butylfuran (40.1 m mol), and tert.butyl chloride (189 m mol) only.

EXAMPLE 2

A 3 liter four-necked flask was fitted with thermometer, paddle stirrer and two condensers, both single walled and mounted one on top of the other. Iron (III) oxide (40g) was added followed by a mixture (790 ml) containing furan (68g), tert.butyl chloride (185g) and 1,1,1-trichloroethane (500 ml). The mixture was stirred vigorously and heated to reflux (60° C.). Iron (III) chloride (4.0g) was then added. After about 15 minutes there was a vigorous reaction. The temperature of the mixture rose to 70° C. and even with the two condensers in series some clear liquids spilled from the top of the upper condenser and were lost. The mixture was kept at reflux temperature for about 60 minutes after the onset of the vigorous reaction and it was then allowed to cool. There remained 700 ml of liquid which glc analysis showed to contain 2,5-di-tert.butylfuran(63 g).

The liquid was subjected to fractional distillation under water pump vacuum (15 mm Hg). A fraction (60g) distilling at 75°–82° C. had an infra-red spectrum nearly identical to that of an authentic sample of 2,5-di-tert.butylfuran. There remained in the distillation flask a non-distillable residue (137g).

EXAMPLE 3

Dichloromethane (1275 g), iron (III) oxide (200 g) and iron (III) cloride (5.0 g) were charged to a reaction vessel and the stirred mixture was heated to reflux temperature (ca. 40° C.). A mixture of furan (85.1 g) and tert.butyl chloride (289.3 g) was then run into the solvent/catalyst mixture during about 1.5 hours, and the mixture was then maintained at reflux temperature, with stirring, for a further 1.5 hours after the addition was complete. The reaction mixture was then filtered to remove the catalyst, which was washed on the filter with dichloromethane (2×100 g). The filtrate and washings were combined and the dichloromethane was distilled off until the internal temperature of the mixture reached 60°-65° C. Glycerol (125 g) was then added and the mixture was subjected to distillation under reduced pressure to give 2,5-di-tert.butylfuran (80 g at 85.9% strength=32% of theoretical based on furan charged) b.p. 85° C./15 mm Hg pressure (20 mbar).

I claim:

1. A process for the preparation of alkylfurans which comprises reacting furan with an alkyl halide in the presence of iron (III) oxide and an iron (II) halide or iron (III) halide as catalyst.

2. A process as claimed in claim 1 wherein the amount of iron (III) oxide which is used is from 0.01 to 2.0 mols per mol of furan.

3. A process as claimed in claim 1 or claim 2 wherein the amount of iron (II) halide or iron (III) halide which is used is from 0.01 to 0.05 mols per mol of furan.

4. A process as claimed in any one of claims 1 to 3 wherein there is used 1.0 mol of iron (III) oxide and 0.025 mol of iron (II) halide or iron (III) halide per mol of furan.

5. A process as claimed in any one of claims 1 to 4 wherein the iron halide is iron (III) chloride.

6. A process as claimed in any one of claims 1 to 5 wherein the reaction is carried out in the presence of a halogenated hydrocarbon solvent.

7. A process as claimed in claim 6 wherein the furan and the alkyl halide are mixed together and added gradually to the catalyst suspended in the solvent at the reaction temperature.

* * * * *